(12) United States Patent
Jach

(10) Patent No.: US 6,642,835 B2
(45) Date of Patent: *Nov. 4, 2003

(54) CERAMIC LAYER SYSTEM AND METHOD FOR PRODUCING A CERAMIC HEATING DEVICE

(75) Inventor: Olaf Jach, Boeblingen (DE)

(73) Assignee: Robert Bosch GmbH, Stuttgart (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/600,092

(22) PCT Filed: Sep. 28, 1999

(86) PCT No.: PCT/DE99/03112
§ 371 (c)(1),
(2), (4) Date: Aug. 30, 2000

(87) PCT Pub. No.: WO00/28785
PCT Pub. Date: May 18, 2000

(65) Prior Publication Data
US 2003/0076218 A1 Apr. 24, 2003

(30) Foreign Application Priority Data
Nov. 11, 1998 (DE) .......................... 198 51 966

(51) Int. Cl.[7] .............................. H01C 1/012
(52) U.S. Cl. ........................ 338/307; 338/195
(58) Field of Search ..................... 338/195, 25

(56) References Cited

U.S. PATENT DOCUMENTS

| | | | | |
|---|---|---|---|---|
| 3,512,254 A | * | 5/1970 | Jenkins ................. | 338/25 |
| 4,332,081 A | * | 6/1982 | Francis ................. | 29/612 |
| 4,375,056 A | * | 2/1983 | Baxter et al. .......... | 338/25 |
| 4,464,244 A | | 8/1984 | Uchida et al. | |
| 4,559,126 A | | 12/1985 | Mase et al. | |
| 4,792,779 A | * | 12/1988 | Pond et al. ............ | 338/195 |
| 4,901,051 A | * | 2/1990 | Murata et al. ......... | 338/25 |
| 4,909,078 A | * | 3/1990 | Sittler et al. .......... | 73/204.26 |
| 5,057,811 A | * | 10/1991 | Strott et al. ........... | 338/22 R |
| 5,557,252 A | * | 9/1996 | Ariyoshi ................ | 338/195 |
| 5,815,065 A | * | 9/1998 | Hanamura ............. | 338/309 |
| 6,004,471 A | * | 12/1999 | Chuang ................. | 216/16 |
| 6,304,167 B1 | * | 10/2001 | Nakayama ............ | 338/195 |

FOREIGN PATENT DOCUMENTS

| | | | | |
|---|---|---|---|---|
| DE | 3021288 | * | 6/1980 | ........... 338/195 |
| DE | 195 22 347 | | 9/1996 | |
| GB | 1474731 | * | 5/1977 | ........... 338/195 |

* cited by examiner

Primary Examiner—Karl D. Easthom
(74) Attorney, Agent, or Firm—Kenyon & Kenyon

(57) ABSTRACT

A ceramic composite having at least one electrical resistor run integrated into the ceramic composite, with the composite including at least one layer that covers the resistor run toward the outside.

The layer covering the resistor run has at least one opening through which the resistor run can be trimmed.

5 Claims, 1 Drawing Sheet

CERAMIC LAYER SYSTEM AND METHOD FOR PRODUCING A CERAMIC HEATING DEVICE

The present invention relates to a ceramic composite having the features given in the preamble of claim 1 as well as a method for producing a ceramic heating element having the features given in the preamble of patent claim 7.

BACKGROUND INFORMATION

Ceramic composites of the type according to the definition of the species are used, for example, for ceramic heating elements in electrochemical sensors. For this purpose, meander-patterned electrical resistor runs are provided and used to form a ceramic heating element. Electrochemical sensors of this type make it possible to measure an oxygen concentration in an exhaust gas of internal combustion engines to select the setting of a fuel/air mixture for operating the internal combustion engine. In the active range, the sensors must be heated to temperatures above roughly 300° C. to achieve the necessary ion conductivity of a solid electrolyte. The ceramic heating element integrated into the electrochemical sensor is used for this purpose.

The production of sensors of this type in the form of planar lambda probes, using a layer technique, is known. To do this, individual layers are arranged on top of each other and possibly patterned. This layer construction is obtained, for example, by sheet casting, stamping, screen-printing, lamination, cutting, sintering or similar methods. The heating element—in particular, the meandering electrical resistor runs that form the heating element—is constructed in the same manner. To prevent reductions in adjacent layers, or to suppress leakage currents, the heating element must be shielded by providing an insulating layer.

To increase sensor measurement accuracy, known methods involve the control and possibly adjustment of the sensor operating temperature. In known methods, the heating element is assigned a measuring element via which the heating element can be engaged and disengaged, respectively, as a function of a measured operating temperature. The heating element resistance (according to the present invention, this resistance is the internal electrical resistance of one electrical conductor of the heating element) must lie within narrow tolerances to prevent heating element overloading and underloading, respectively. Otherwise, the detected measured value would be corrupted.

The heating element resistance has proven to vary by an especially large amount in the region of its meandering pattern, due to the manufacturing process. The resistance depends on the temperature, resistance coefficients of the material used, and the length of the heating element conductors. For production reasons, the composition, and thus the resistance coefficient, of individual conductor areas in the heating element can vary, and the heating element conductors may also vary in length. It is not possible to trim the resistance in previously known methods. Consequently, sensors whose resistance proves to be unusable for the heating element during the first measurement must be discarded.

The embodiment described above by way of an example, in which the ceramic heating element forms part of the sensing element of a sensor to measure an oxygen concentration, serves only to explain the disadvantages of the related art. These disadvantages also arise in other applications that use a resistor meander integrated into a ceramic composite. Such examples can include temperature sensors or passive sensors that respond to resistance changes in media. These applications also require a defined resistance of an electrical resistor run.

ADVANTAGES OF THE INVENTION

The ceramic composite according to the present invention having the features given in claim 1 provides the advantage that it includes an integrated electrical resistor run that has a defined, reproducible electrical resistance. Because the layer covering the resistor run has at least one opening through which the resistor run can be trimmed, it is possible to set the resistance of the resistor run at a later time, i.e., after patterning the ceramic composite. The resistor run, which is preferably designed as a resistor meander, has junctions and/or sealed zones (also referred to hereinafter as seal zones, zones, and filled zones) at least in the area of adjacent conductor segments, with the resistance of the resistor run being adjustable by cutting the junctions and/or zones. In an embodiment of this type, a pattern that supports subsequent trimming of the resistor run resistance can be integrated with an easily reproducible layout into the ceramic composite. The junctions and/or sealed zones between adjacent conductor segments are made of the same resistive material as the resistor runs and are patterned together with the latter, in particular, by screen-printing or a similar technique.

The method according to the present invention for producing a ceramic heating element having the features given in claim 7 has the advantage that it can be used to provide mass-produced ceramic heating elements that have a uniform heating meander resistance. Because the electrical resistance of the heating meander is set after sintering the composite, with an effective length of a conductor forming the heating meander preferably being adjusted subsequently, production-related tolerances in the heating meander resistance can be easily equalized. When using such ceramic heating elements according to specification, it is therefore possible, in particular, to combine the heating elements with a measurement and control circuit, thus providing a precise, defined, and reproducible heating meander resistance for the measurement and control circuit. As a result, it is possible to achieve uniform measurement and control results when the ceramic heating elements are mass-produced, since production-related resistance fluctuations that would lead to deviations in the measurement and control results are eliminated.

A preferred application is to use the ceramic composite having the features given in claim 1 as a heating element in a sensing element of an electrochemical sensor, in particular for measuring an oxygen concentration in the exhaust gas of internal combustion engines.

Up to the layer containing the heating element, the sensor is constructed in the known manner by sheet casting, stamping, screen-printing, lamination, cutting, sintering or similar methods. The heating element conductor has junctions and/or filled zones between the individual meander windings in the area with the meandering pattern. The subsequent layers have openings in these exact areas.

After the layers needed to operate the sensor have been applied, the resistance of the heating meander can be trimmed, preferably using a laser, by correcting the length of the heating meander conductors correspondingly. This can be easily accomplished by using a laser to cut or trim the junctions and/or sealed zones between adjacent conductor segments in the heating meander. The openings are then sealed air-tight, for example by glazing. The openings through which laser cutting or laser trimming is carried out are then sealed with a filler, in particular by glazing them with a ceramic glass.

In a preferred embodiment of the present invention, the layers covering the heating element can be designed so that the laser can pass through them to cut or trim the junctions and/or filled zones. As a result of the heat applied to the layer covering the heating meander during laser treatment, heating meanders can be easily glazed at the same time, with these layers containing glazing agents for this purpose.

Further preferred embodiments of the present invention are derived from the remaining features given in the subclaims.

DRAWINGS

The present invention is explained in greater detail below on the basis of embodiments illustrated in the associated drawings, where:

DESCRIPTION OF THE EMBODIMENTS

Figure 1:
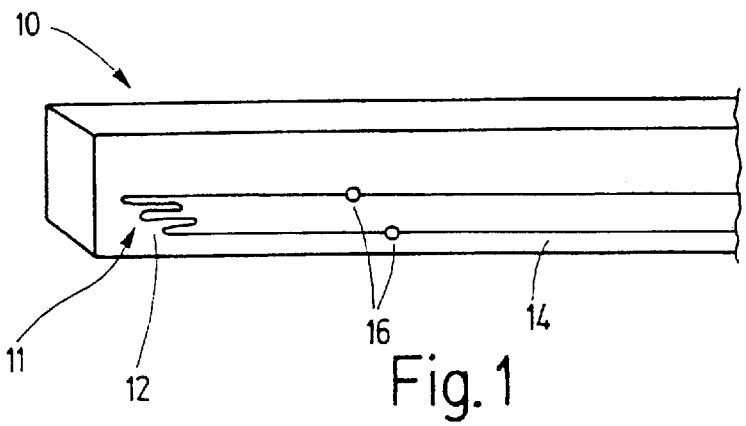
FIG. 1 shows a schematic perspective view of a composite.

FIG. 1 shows a schematic representation of the layer containing a heating element 11 in a composite 10. Heating element 11 includes conductors 14 that are connected by points of contact 16 to a meander-shaped structure of heating element 11, referred to below as resistor meander 12. A composite 10 of this type is produced in layers, for example by sheet casting, stamping, screen-printing, lamination, cutting or sintering.

Composites 10 of this type form part, for example, of sensors that can be used to detect gas components in an exhaust gas of internal combustion engines of motor vehicles. Composites 10 can also form part of temperature sensors. It is also conceivable to use them in sensors that respond to resistance changes in the presence of certain media (gases, fluids or similar media). To guarantee a functionality of this type, the sensors have additional components which will not be discussed in any further detail here. In a sensor of this type, composite 10 would then represent a sensing element.

Figures 2A, 2B:
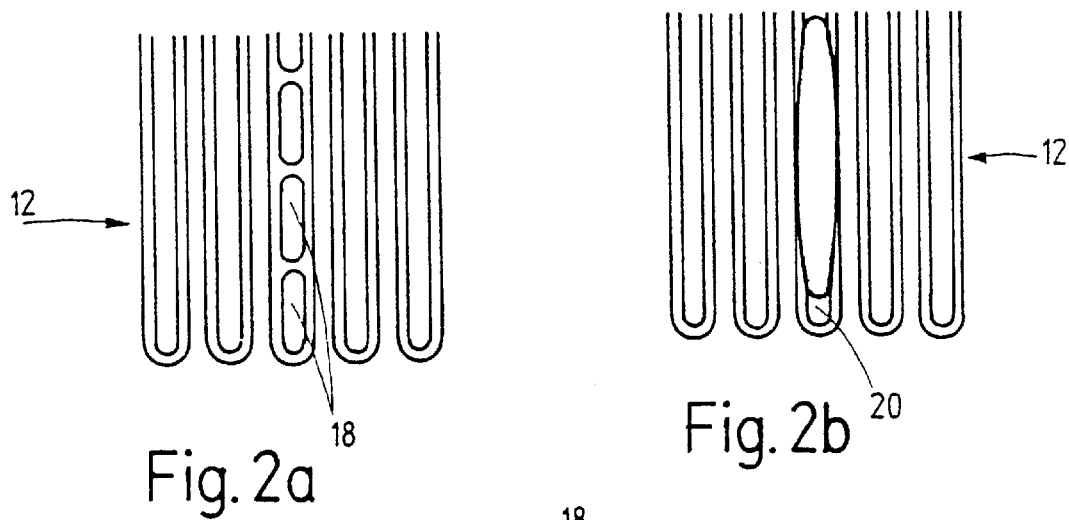
FIGS. 2a and 2b show two embodiments of a heating meander.

FIGS. 2a and 2b show two embodiments of resistor meander 12. Between two adjacent windings of meander 12, junctions 18 (FIG. 2a) and/or filled zones 20 (FIG. 2b) are formed from the same material as conductors 14. The layer containing the heating element is produced in an essentially known manner, for example by screen-printing conductors 14. Resistor meander 12 is usually made of a conductive metal, an alloy, or a CERMET.

Figure 3:
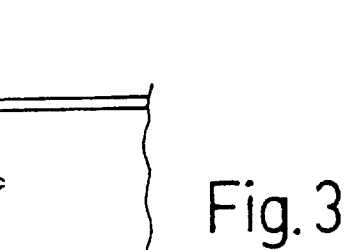
FIG. 3 shows a schematic representation of a composite, viewed from above.

FIG. 3 shows a schematic representation, viewed from above, of a composite 10 having an opening 22. Resistor meander 12, or specifically the areas of resistor meander 12 in which individual windings are connected by junctions 18 or filled zones 20, is located at the base of opening 22.

Figures 4A, 4B:
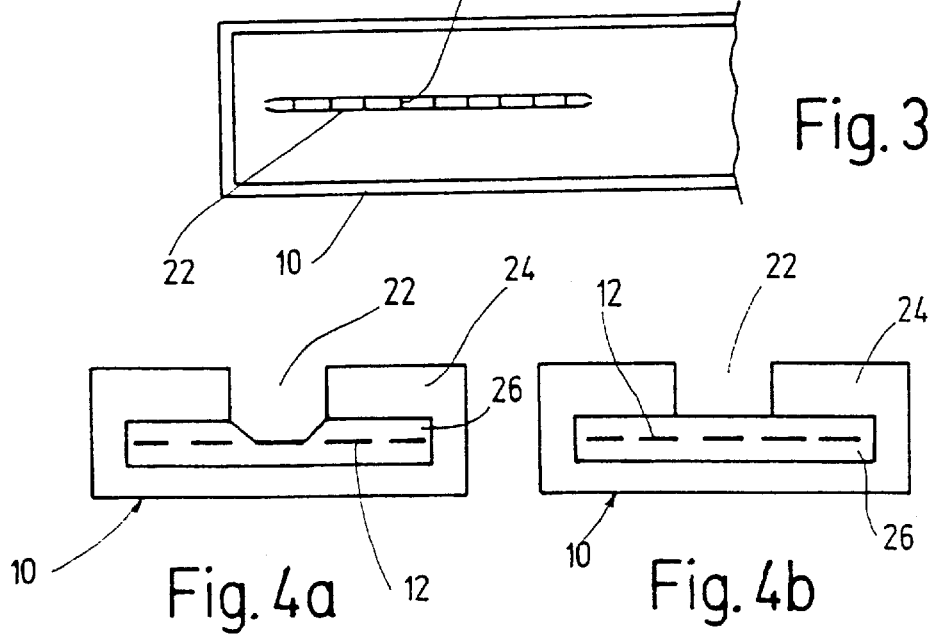
FIGS. 4a and 4b show schematic cross-sectional views of composites.

FIGS. 4a and 4b show a schematic cross-sectional view of composite 10. The heating element in this case is usually shielded from a layer 24 by an insulating layer 26 to prevent a reduction in layer 24 or a leakage current flow. Resistor meander 12 can be worked through opening 22.

Composite 10 shown in FIG. 4a can be preferably produced by the following steps. Heating element 11, which contains resistor meander 12 and its junctions 18 or filled zones 20, is first produced according to the usual method. Insulating layer 26 contains opening 22 in the areas where junctions 18 or filled zones 20 of meander 12 are located. Likewise, all subsequent layers, normally a final protective layer, are modified so that they also have a matching opening 22.

In a further preferred embodiment of composite 10 illustrated in FIG. 4b, insulating layer 26 also covers the areas of opening 22. Insulating layer 26 is designed so that a laser can penetrate this layer 26, making it possible to trim resistor meander 12. In doing so, the thermal action of the laser also causes this layer 26 to be glazed. Layer 26 contains corresponding glazing agents for this purpose.

Resistor meander 12 can now be trimmed by a laser as follows. Junctions 18 or filled zones 20 accessible through opening 22 are severed, i.e., trimmed, by cutting them with the laser.

During this process, the change in resistance of heating element 11 can be tracked by a circuit arrangement that is not described in any further detail here. Laser cutting, i.e., laser trimming, increases the resistance by increasing the length of conductors 14. Composites 10 that have identical internal resistance values of resistor meander 12 can be produced in this manner.

Opening 22 is sealed by a filler after laser trimming, preferably by glazing it with a ceramic glass. This makes it possible to protect heating element 11 against mechanical or chemical influences.

What is claimed is:

1. A ceramic composite, comprising:
   at least one integrated electrical resistor run forming a meandering pattern; and
   at least one layer covering the at least one electrical resistor run toward an outside, the at least one layer having at least one opening through which the at least one electrical resistor run may be trimmed, wherein:
   the at least one integrated electrical resistor run has at least one of junctions and seal zones at least between adjacent conductor segments in an area of the meandering pattern, a resistance of the at least one integrated electrical resistor run being adjustable by cutting at the at least one of junctions and seal zones, and
   the at least one of junctions and seal zones are situated in an area of the at least one opening and include a same resistive material as the at least one integrated electrical resistor run.

2. The composite according to claim 1, wherein:
   the at least one opening may be sealed with a filler after the at least one integrated electrical resistor has been trimmed.

3. The composite according to claim 2, wherein:
   the filler includes ceramic glass.

4. The composite according to claim 1, wherein:
   the composite is a measuring resistor in a sensing element of a temperature sensor.

5. The composite according to claim 1, wherein:
   a width between adjacent conductor segments of the at least one integrated resistor run at a location of the at least one of junctions and seal zones is the same as a width between adjacent conductor segments of the at least one integrated resistor run where the at least one of junctions and seal zones are absent.

* * * * *

UNITED STATES PATENT AND TRADEMARK OFFICE
CERTIFICATE OF CORRECTION

PATENT NO. : 6,642,835 B2
DATED : November 4, 2003
INVENTOR(S) : Olaf Jach

It is certified that error appears in the above-identified patent and that said Letters Patent is hereby corrected as shown below:

Title page,
Item [57], ABSTRACT,
Line 1, change "having" to -- including --;
Lines 2-3, change "with the composite" to -- and --;
Line 3, delete "including";

Column 1,
Line 4, insert -- FIELD OF THE INVENTION --;
Lines 6-7, change "having the features given in the preamble of claim 1 as well as a" to -- and a --;
Lines 7-8, change "element having the features given in the preamble of patent claim 7." to -- element. --;
Lines 11-12, delete "of the type according to the definition of the species";
Line 14, change "meander-patterned" to -- meandrous-patterned --;
Lines 25, 36 and 38, change "known" to -- conventional --;
Delete line 48 and insert -- Due to the manufacturing process, the heating element resistance varies by an --;
Line 49, change "meandering" to -- meandrous --;
Line 50, delete ", due to the manufacturing process";
Line 57, change "previously known" to -- conventional --;
Line 65, change "related art" to -- conventional methods --;
Line 66, change "resistor meander" to -- meandrous resistor run --;

Column 2,
Line 5, change "ADVANTAGES " to -- SUMMARY --;
Line 7, delete "having the features given in Claim 1";
Line 14, change "is preferably designed as a resistor meander" to -- is, for example, designed as a meandrous resistor run --;
Line 29, delete "having the features given in Claim 7";
Lines 32, 36, 41 and 63, change "heating meander" to -- meandrous heating --;
Lines 33, 35, 61 and 66, change "heating meander" to -- meandrous heating element --;
Line 35, delete "preferably";
Line 48, change "A preferred" to -- An advantageous --;
Line 49, change "having the features given in Claim 1" to -- according to the present invention --;
Line 54, change "the known" to -- a conventional --;
Line 57, change "meander" to -- meandrous --;
Line 58, change "meandering" to -- meandrous --;
Line 62, change "preferably" to -- for example --;

UNITED STATES PATENT AND TRADEMARK OFFICE
CERTIFICATE OF CORRECTION

PATENT NO. : 6,642,835 B2
DATED : November 4, 2003
INVENTOR(S) : Olaf Jach

It is certified that error appears in the above-identified patent and that said Letters Patent is hereby corrected as shown below:

Column 3,
Line 1, change "carried out" to -- performed --;
Line 4, change "a preferred" to -- an advantageous --;
Line 8, change "heating meander" to -- meandrous heating element --, and change "heating" (second occurrence) to -- meandrous heating elements --;
Line 9, delete "meanders";
Delete lines 15-29, and insert
-- BRIEF DESCRIPTION OF THE DRAWINGS Figure 1 shows a schematic perspective view of a composite.
Figure 2a shows a first embodiment of a meandrous heating element.
Figure 2b shows a second embodiment of a meandrous heating element.
Figure 3 shows a top view of a schematic representation of a composite.
Figure 4a shows a cross sectional schematic view of a first embodiment of a composite.
Figure 4b shows a cross sectional schematic view of a second embodiment of a composite.
DETAILED DESCRIPTION --;
Line 33, change "meander-shaped" to -- meandrous-shaped --;
Lines 34 and 60, change "resistor meander" to -- meandrous resistor run --;
Line 47, change "discussed" to -- described --;
Line 48, delete "then";
Line 50, change "resistor meander" to -- meandrous resistor run --;
Line 51, change "meander" to -- meandrous resistor run --;
Line 55, change "known" to -- conventional --;
Lines 56 and 59, change "Resistor meander" to -- Meandrous resistor run --;
Line 66, change "Resistor" to -- Meandrous resistor run --;
Line 67, delete "meander";

UNITED STATES PATENT AND TRADEMARK OFFICE
CERTIFICATE OF CORRECTION

PATENT NO. : 6,642,835 B2
DATED : November 4, 2003
INVENTOR(S) : Olaf Jach

It is certified that error appears in the above-identified patent and that said Letters Patent is hereby corrected as shown below:

Column 4,
Line 1, change "preferably produced" to -- produced, for example, --;
Lines 3, 13 and 25, change "resistor meander" to -- meandrous resistor run --;
Line 4, change "the usual" to -- a conventional --;
Line 6, change "meander" to -- meandrous resistor run --;
Line 10, change "preferred" to -- advantageous --;
Line 17, change "Resistor meander" to -- Meandrous resistor run --; and
Line 28, change "preferably" to -- for example--.

Signed and Sealed this

Fifteenth Day of February, 2005

JON W. DUDAS
*Director of the United States Patent and Trademark Office*